United States Patent [19]
Kato et al.

[11] Patent Number: 5,302,276
[45] Date of Patent: Apr. 12, 1994

[54] ELECTROCHEMICAL ELEMENT

[75] Inventors: Nobuhide Kato, Aichi; Hitoshi Nishizawa, Iwakura; Toshihiko Suzuki, Nagoya, all of Japan

[73] Assignee: NGK Insulators, Ltd., Nagoya, Japan

[21] Appl. No.: 832,340

[22] Filed: Feb. 7, 1992

[30] Foreign Application Priority Data

Mar. 29, 1991 [JP] Japan .................................. 3-93456

[51] Int. Cl.⁵ .................................. G01N 27/417
[52] U.S. Cl. .................................. 204/429; 204/426
[58] Field of Search .................. 204/153.18, 421–429

[56] References Cited
U.S. PATENT DOCUMENTS

| | | | |
|---|---|---|---|
| 3,843,400 | 10/1974 | Radford et al. | 204/427 |
| 4,101,403 | 7/1978 | Kita et al. | 204/429 |
| 4,220,516 | 9/1980 | Sano et al. | 204/429 |
| 4,505,807 | 3/1985 | Yamada | 204/427 |
| 4,626,337 | 12/1986 | Hotta et al. | 204/429 |
| 4,668,375 | 5/1987 | Kato et al. | 204/425 |
| 5,110,442 | 5/1992 | Kojima et al. | 204/426 |

*Primary Examiner*—T. Tung
*Attorney, Agent, or Firm*—Adduci, Mastriani, Schaumberg & Schill

[57] ABSTRACT

A solid electrolyte is interposed between a first electrode layer located while in contact with the gas to be measured and a second electrode layer located while in contact with a reference gas. The first electrode layer is covered on its high-temperature portion with a first porous protecting layer and on its low-temperature portion with a second porous protecting layer which is lower in gas permeability than the first porous protecting layer. This electrochemical element can be produced without detriment to the porous protecting layers, e.g., causing them to peel off or crack. In addition, it can be used while any lowering of insulating resistance between the first electrode layer and the associated metal holder, thereby providing an accurate detection of the concentration of a specific gas in the gas to be measured.

6 Claims, 5 Drawing Sheets

Gas To Be Measured
(Exhaust Gas)

Reference Gas
(Air)

Gas To Be Measured (Exhaust Gas)     Reference Gas (Air)

Gas To Be Measured (Exhaust Gas)     Reference Gas (Air)

Gas To Be Measured (Exhaust Gas)

Reference Gas (Air)

Gas To Be Measured (Exhast Gas)

Reference Gas (Air)

ELECTROCHEMICAL ELEMENT

BACKGROUND OF THE INVENTION

This invention relates to an electrochemical element in general and to an oxygen sensor element in particular, which is used to determine the concentration of oxygen contained in exhaust gases from an internal combustion engine, for instance.

So far, there has been known an electrochemical sensor element including first and second electrode layers and a solid electrolyte, wherein the first and second electrode layers are brought into contact with the gas to be measured and a reference gas, respectively, whereby a potential difference between the first and second electrode layers is found to determine the concentration of a specific component, e.g., oxygen, in the gas to be measured.

One typical oxygen sensor is set forth in Japanese Patent Kokai Publication No. 60(1985)-36948, and includes a first electrode layer which is covered on its portion to contact the gas to be measured with a single porous protecting layer. Another oxygen sensor is set forth in Japanese Patent Kokai Publication No. 60(1985)-36949, and includes a first electrode layer which is covered on high- and low-temperatures regions of its portion to contact with the gas to be measured with a porous protecting layer and an air-tight protecting layer, respectively.

However, a problem with the oxygen sensor having the first electrode layer covered with a single protecting layer is that when the porous protecting layer has an increased gas permeability, carbon is likely to accumulate on and in it and in the first electrode layer while the internal combustion engine operates under conditions rich in fuel or, in other words, exhaust gas conditions poor in oxygen, giving rise to a lowering of insulation resistance between the first electrode layer and the metal holder of the oxygen sensor. In particular, this decrease in insulation resistance become more serious when carbon deposition takes place on the low-temperature region of the porous protecting layer or the first electrode layer in an arrangement where the first electrode layer lies relatively close to the metal holder.

A problem with the process of producing the oxygen sensor set forth in Japanese Patent Kokai Publication No. 60-36949 is that when the oxygen sensor element is immersed in a solution, the solution penetrates through the porous electrode layer so that it is evaporated (gasified) rapidly during baking; that is, if a portion of the protecting layer covering the first electrode layer is air tight, then the gas to be evaporated is so confined within the pores in the first electrode layer that the internal pressure of the first electrode layer increases, causing the protecting layer to peel off or crack.

This invention seeks to provide a solution to the above problems and has for its object to provide an electrochemical element which can be produced without detriment to the porous protecting layer or, in other words, without causing it to peel off and crack, and which can be used while any lowering of insulation resistance between the first electrode layer and the metal holder is avoided, thereby providing an accurate detection of the concentration of a specific component in the gas to be measured.

SUMMARY OF THE INVENTION

According to one aspect of this invention, there is provided an electrochemical element including a first electrode layer located to contact the gas to be measured, a second electrode layer located contact a reference gas and a solid electrolyte interposed between said first and second electrode layers, characterized in that said first electrode layer is covered on its high-temperature portion with a first porous protecting layer and on its low-temperature portion with a second porous protecting layer that is lower in gas permeability than said first porous protecting layer.

It is desired that the second porous protecting layer have a gas permeability lying in the range of 0.005 to 16 $mA/mm^2$ per % of the concentration of oxygen in the gas to be measured.

The first and second porous protecting layers may be made up of a plurality of porous layers having different porosities.

According to another aspect of this invention, there is provided an electrochemical, element including a first electrode layer located to contact the gas to be measured, a second electrode layer located to contact a reference gas and a solid electrolyte interposed between said first and second electrode layers, characterized in that a high-temperature portion of said first electrode layer comprises a cermet consisting of metal particles and a solid electrolyte particles and comes into contact with said solid electrolyte, and a low-temperature portion of said first electrode layer comprises a cermet consisting of metal particles and insulating ceramic particles and is insulated from said solid electrolyte.

According to the second aspect of this invention, the protecting layer covering the first electrode layer may include an insulating ceramic layer in contact with the low-temperature portion of the first electrode layer.

As mentioned above, the low-temperature portion of the protecting layer covering the first electrode layer is regulated to a density giving a predetermined range of gas permeabilities; that is, the electrochemical element according to this invention can be produced without detriment to the porous protecting and electrode layers, e.g., without causing them to crack, and can be used while any carbon deposition is prevented, thereby avoiding any lowering of insulation resistance between the first electrode layer and the associated metal holder.

Further, the ceramic component of the low-temperature portion of the first electrode layer is formed of the same insulating ceramics as the underlying insulating ceramic layer, thereby improving the adhesion strength of the low-temperature portion of the first electrode layer to the insulating ceramic layers. Alternatively, the proportion of the ceramic component in the low-temperature portion (underlying layer) of the first electrode layer is increased, thereby improving the adhesion strength of the low-temperature portion of the first electrode layer to the solid electrolyte. Thus the electrochemical element according to this invention can be produced and used without detriment to the electrode layers, e.g., causing them to crack.

BRIEF DESCRIPTION OF THE DRAWINGS

This invention will now be explained more specifically but not exclusively with reference to the accompanying drawings, in which.

PREFERRED EMBODIMENT OF THE INVENTION

In what follows, this invention will be explained with reference to some preferred examples of the invention.

A paste prepared by mixing 90% by weight of platinum and 10% by weight of zirconia with an organic binder and a solvent was formed on both sides of a solid electrolyte green sheet consisting of zirconia by screen printing to make first and second electrode layers. A paste consisting of zirconia is coated on the surface of the first electrode layer by screen printing to form first and second porous protecting layers. Four sheets, i.e., this green sheet; a zirconia green sheet which is located in opposite relation to said green sheet, providing a porous zirconia layer forming parts of the first and second porous protecting layers; a zirconia green sheet including a cutout defining a reference gas duct; and a zirconia green sheet including a heater layer formed, by sandwiching a heat-generating pattern consisting of 90% by weight of platinum and 10% by weight of alumina between alumina layers;—all are thermally bonded together, cut and formed into an integral green sheet assembly. This green sheet assembly was calcined at 1400° C. in the air for 3 hours to obtain an electrochemical element shown in FIG. 1.

Figure 1:
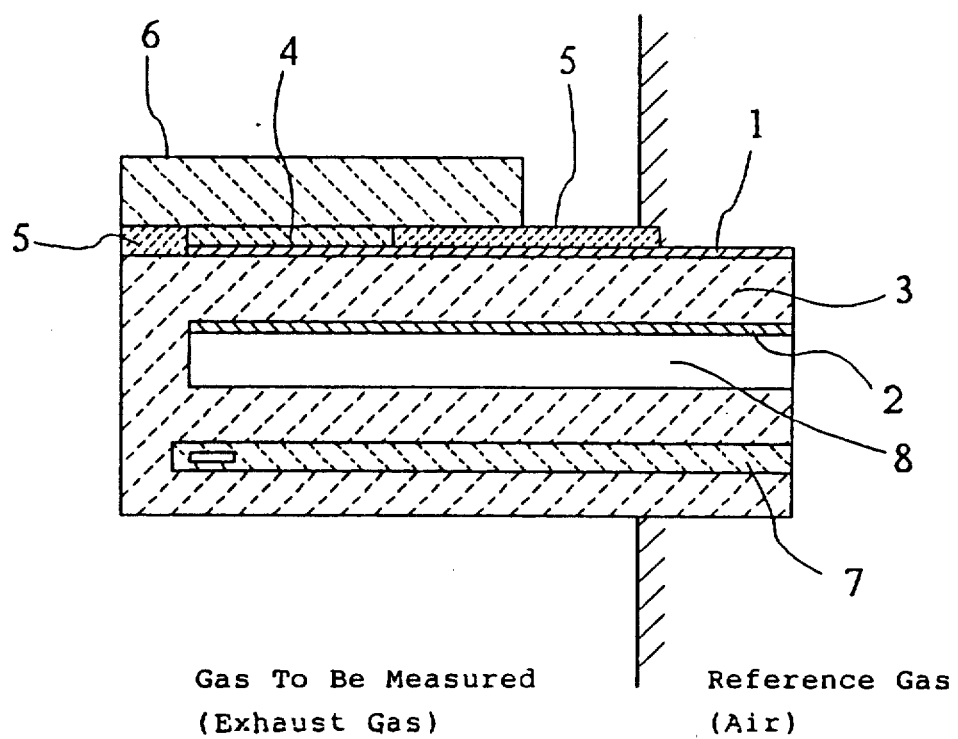
FIG. 1 is a schematic view of a 1st example of this invention.

Referring to the first example shown in FIG. 1, a first electrode layer 1 is provided on its high-temperature portion with a first porous protecting layer 4 and on its low-temperature portion with a second porous protecting layer 5. Then, the first and second porous protecting layers 4 and 5 on the high- and low-temperature portions are provided on their surfaces with a third porous protecting layer 6 that is well permeable to gas. The second electrode layer 2 includes a cavity 8 to come into contact with a reference gas, and a solid electrolyte 3 has a ceramic heater 7 embedded in it.

Here, the gas permeability of the second porous protecting layer 5 may be regulated as by varying the amount of the binder to be added to the zirconia paste or changing the particle size of the starting zirconia feed.

Next, a number of samples, some according to this invention and some for comparative purposes, were prepared by varying the gas permeability of the second porous protecting layer, and these were used for both rapid heating tests and rich-in-air mode continuous operating tests.

The results are set out in Table 1.

TABLE 1

|  | A | B | C |
|---|---|---|---|
| Comparative Example | | | |
| 1 | 0.00016 | 6.66 | — |
| 2 | 0.0018 | 3.33 | — |
| Example | | | |
| 1 | 0.005 | 0 | — |
| 2 | 0.019 | 0 | — |

TABLE 1-continued

|  | A | B | C |
|---|---|---|---|
| 3 | 0.034 | 0 | — |
| 4 | 0.092 | 0 | — |
| 5 | 0.27 | 0 | — |
| 6 | 0.34 | 0 | — |
| 7 | 0.89 | 0 | — |
| 8 | 3.8 | — | 0 |
| 9 | 5.1 | 0 | — |
| 10 | 7.9 | 0 | 0 |
| 11 | 15.8 | — | 0 |
| Comparative Example | | | |
| 3 | 42 | — | 33.3 |

A: Gas Permeability of the 2nd Porous Protecting Layer in mA/mm $O_2$ %.
B: Percentage of Defects in Rapid Heating Tests in %.
C: Percentage of Defects in Rich-In-Air Mode Continuous Operating Tests in %.

The tests were carried out under following conditions.

GAS PERMEABILITY TESTS

The gas permeability of each of the second porous protecting layers was measured as follows. While the electrochemical element was locally heated at its middle portion (or, in actual use, its low-temperature portion) to 700° C. by a separately provided ceramic heater, a current was supplied from an external d.c. source through the second electrode layer 2 to the first electrode layer 1 in an atmosphere containing the gas to be measured, which was diluted by nitrogen to an oxygen concentration of 0.1 to 20%, to pump oxygen ions from the first electrode layer 1 to the second electrode layer 2, thereby measuring the diffusion limiting current which, in this case, was found in terms of a current value per unit area of the first electrode layer per % of the concentration of heated oxygen. For instance, when the concentration of oxygen was 0.5%, the value of the diffusion limiting current per unit area was doubled.

Rapid Heating Tests

Thirty (30) samples of varied grades were each boiled in boiling water of 100° C. for 10 minutes to impregnate the pores in the first electrode layer with water. After that, water was wiped from the surface of the sample, which was then heated at a maximum heating rate of 100° C./sec at a maximum temperature of 1,000° C. with the use of a gas burner to examine to what degree the first and second porous protecting layers peeled off—the percentage of defects. As can be clearly seen from Table 1, no peeling of the protecting layers was found at all in Examples 1-7, 9 and 10, but some peeling of the protecting layers was observed in Comparative Examples 1 and 2.

Rich-In-Air Mode Continuous Operating Tests

Six (6) samples of varying grades were each built in a metal holder, and while a direct current was applied to it at a heater voltage of 12 V, this metal holder was attached to a testing pipe. Then, an exhaust gas obtained by the combustion of propane, which contained excess air as expressed in terms of $\lambda = 0.7$, was passed through this testing pipe for 1,000 hours. After that, the insulation resistance between the first electrode layer and the metal holder was measured to find the percentage of defects which, by definition, have an insulation resistance of 1 kΩ or less. The percentage of defects ensuing from a lowering of insulation resistance is 0 in Examples 8, 10 and 11, but it reaches ⅓ in Comparative Example 3.

Some other forms of the electrochemical elements according to this invention are shown in FIGS. 2, 3, 4 and 5.

Figure 2:
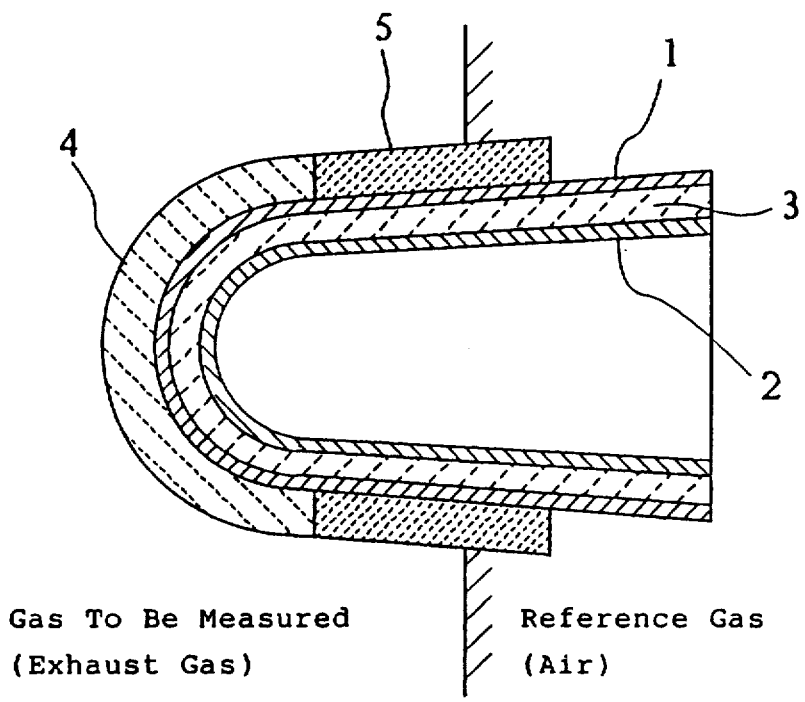
FIG. 2 is a schematic view of a 2nd example of this invention.
Figure 3:
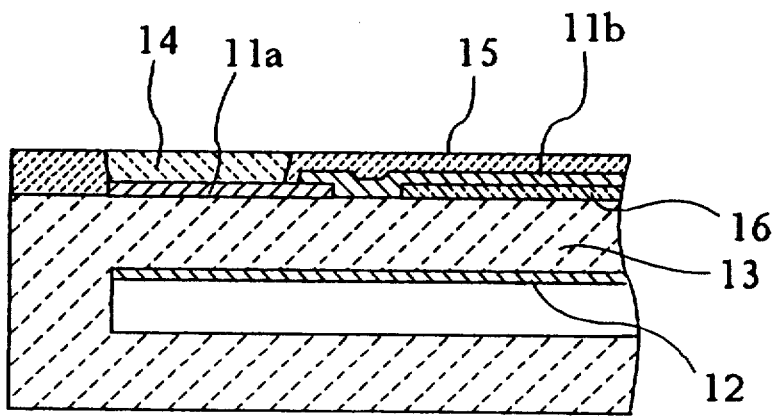
FIG. 3 is a schematic view of a 3rd example of this invention.

According to the 2nd example shown in FIG. 2, a solid electrolyte 3 is formed between the first and second electrode layers 1 and 2. The first electrode layer 1 is provided on its high-temperature portion with a first porous protecting layer 4 and on its low-temperature portion with a second porous protecting layer 5.

According to the 3rd example of this invention, a solid electrolyte 13 is located not only between a first electrode layer 11a forming a high-temperature portion and a second electrode layer 12 but between a first electrode layer 11b forming a low-temperature portion and the second electrode layer 12 as well. Between the first low-temperature electrode layer 11b and the solid electrolyte 13, there is locally provided an insulating ceramic 16. The first high-temperature electrode layer 11a is provided on its surface with a first porous protecting layer 14, while the first low-temperature electrode layer 11b is provided on its surface with a second porous layer 15 that is higher in air-tightness than the first porous protecting layer.

Figure 4:
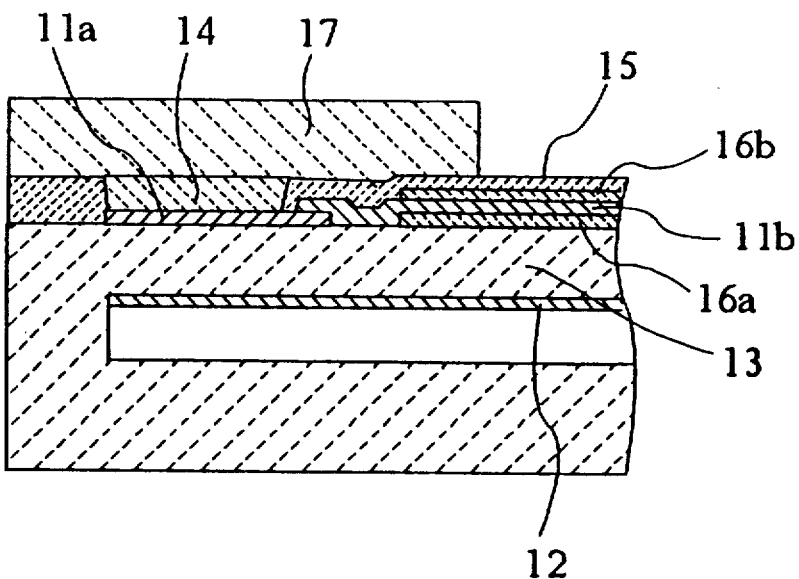
FIG. 4 is a schematic view of a 4th example of this invention.

The 4th example shown in FIG. 4 is similar to the 3rd example with the exception that the first low-temperature electrode layer 11b is provided on a part of its surface with an insulating ceramic layer 16b and another insulating ceramic layer 16a is located between the first low-temperature electrode layer 11b and the solid electrolyte 13. In addition, the first and second porous protecting layers 14 and 15 are provided on high temperature parts of their surfaces with a third porous protecting layer 17.

Figure 5:
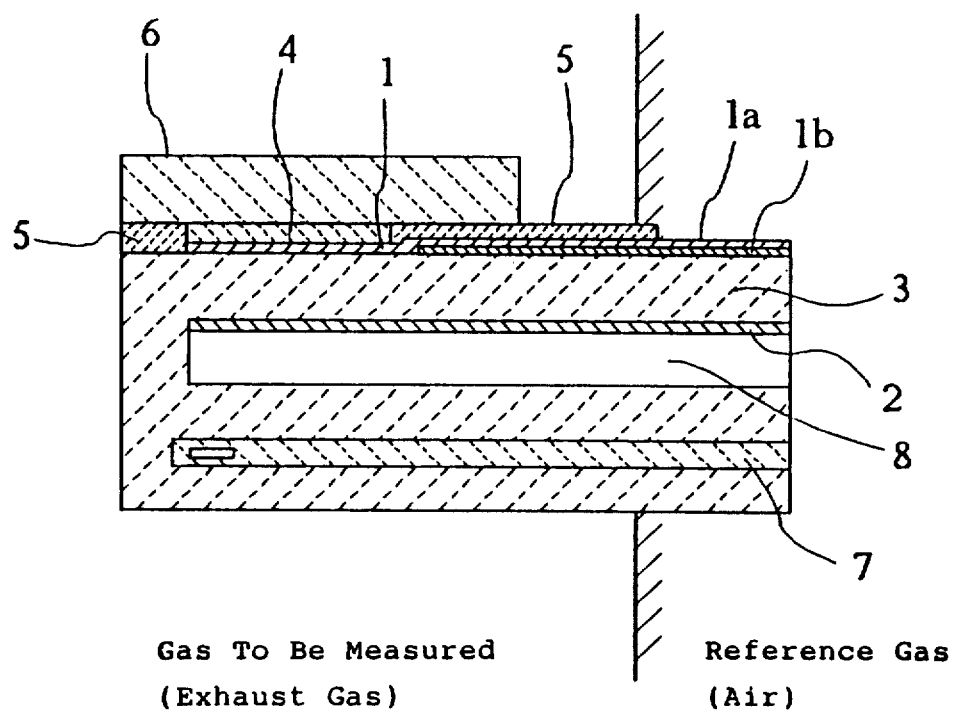
FIG. 5 is a schematic view of a 5th example of this invention.

The 5th embodiment shown in FIG. 5 is similar to the first example with the exception that the low-temperature portion of the first electrode layer 1 is made up of a laminate. In addition, an upper layer 1a of the low-temperature portion is similar in composition to the high-temperature portion of the first electrode layer 1 and a lower layer 1b of the low temperature portion is rich in zirconia or consists of, say, 40 parts by volume of platinum and 60 parts by volume of zirconia.

According to all Examples 1–5, the gas permeability of the second porous protecting layer is regulated to the above-mentioned range. Thus, not only can the electrochemical elements be produced with no fear of their destruction or breaking-down, but they can also be used while carbon deposition in the vicinity of the second porous protecting layer or the electrode layers is sufficiently avoided.

Figure 6:
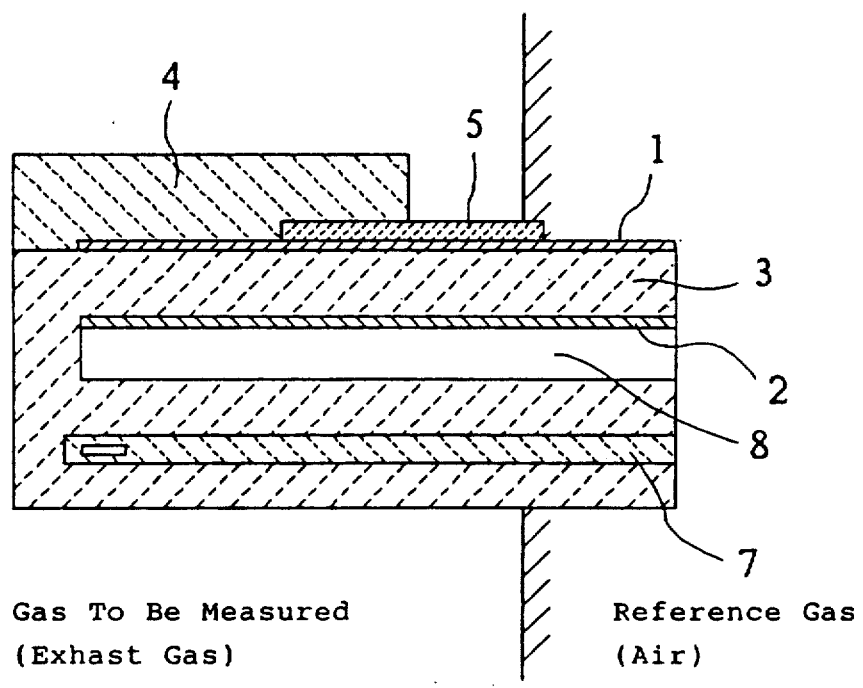
FIG. 6 is a schematic view of a 6th example of this invention.

An electrochemical element according to the 6th embodiment shown in FIG. 6 is built up of a zirconia green sheet providing a zirconia layer on which a first porous protecting layer 4 and a part of a second porous protecting layer 5 are to be formed, and a zirconia layer which forms another part of the second porous protecting layer 5 and is obtained by the screen-printing of a zirconia paste, According to the electrochemical element of this invention, the first electrode layer is covered on its high-temperature portion with the first porous protecting layer and on its low-temperature portion with the second porous protecting layer which is lower in gas permeability than the first porous protecting layer, as explained above; that is, it can be produced without causing the protecting and electrode layers to crack or otherwise break down. In addition, it can be used with no fear of any carbon deposition—because the first electrode layer is well insulated from the solid electrolyte, thereby providing an appropriate detection of the concentration of a specific gas component.

We claim:

1. An electrochemical element including a first electrode layer located to contact gas to be measured, a second electrode layer located to contact a reference gas and a solid electrolyte interposed between said first and second electrode layers, characterized in that said first electrode layer is covered on its high-temperature portion with a first porous protecting layer and on its low-temperature portion with a second porous protecting layer that is lower in gas permeability than said first porous protecting layer.

2. The electrochemical element of claim 1, wherein said high-temperature portion of said first electrode layer comprises a cermet consisting of metal particles and solid electrolyte particles and comes into contact with said solid electrolyte, and a low-temperature portion of said first electrode layer comprises a cermet consisting of metal particles and insulating ceramic particles and is insulated from said solid electrolyte.

3. The electrochemical element of claim 1, wherein said low-temperature portion of said first electrode layer has a multilayer laminate comprising a first layer having a cermet consisting of a metal material that is located on the solid electrolyte side and which is rich in a ceramic component and a second layer that is located on the side of the gas to be measured and rich in a metal component.

4. The electrochemical element of claim 1, further comprising an insulating ceramic layer interposed between the low-temperature portion of said first electrode layer and said solid electrolyte.

5. The electrochemical element of claim 1, further comprising:
a lower insulating ceramic layer interposed between the low-temperature portion of said first electrode layer and said solid electrolyte; and
an upper insulating ceramic layer forming a layer on top of the low-temperature portion of said first electrode layer.

6. The electrochemical element of claim 1, further comprising a third porous protecting layer forming a layer on the top surfaces of both said first and second porous protecting layers, wherein said third porous protecting layer is permeable to gas.

* * * * *